(12) United States Patent
Cho et al.

(10) Patent No.: US 8,948,346 B2
(45) Date of Patent: Feb. 3, 2015

(54) COLLIMATOR AND CONTROL METHOD THEREOF

(75) Inventors: Min Kook Cho, Gyeonggi-do (KR); Seok Mo Ko, Seoul (KR)

(73) Assignee: Samsung Electronics Co., Ltd., Suwon-si, Gyeonggi-do (KR)

(*) Notice: Subject to any disclaimer, the term of this patent is extended or adjusted under 35 U.S.C. 154(b) by 246 days.

(21) Appl. No.: 13/350,962

(22) Filed: Jan. 16, 2012

(65) Prior Publication Data

US 2012/0183126 A1 Jul. 19, 2012

(30) Foreign Application Priority Data

Jan. 17, 2011 (KR) .................. 10-2011-0004558
Jul. 25, 2011 (KR) .................. 10-2011-0073419

(51) Int. Cl.
H05G 1/64 (2006.01)
G21K 1/04 (2006.01)
H05G 1/26 (2006.01)
A61B 6/06 (2006.01)
A61B 6/08 (2006.01)
A61B 6/00 (2006.01)

(52) U.S. Cl.
CPC ... *G21K 1/04* (2013.01); *A61B 6/06* (2013.01); *A61B 6/08* (2013.01); *A61B 6/4035* (2013.01); *A61B 6/469* (2013.01); *A61B 6/54* (2013.01)
USPC ......................... 378/150; 378/98.3; 378/166

(58) Field of Classification Search
USPC ............... 378/91, 98, 98.3, 147, 150–152, 378/162–166, 204–206, 210; 359/443, 449, 359/450, 618, 629, 630, 641, 838, 896
See application file for complete search history.

(56) References Cited

U.S. PATENT DOCUMENTS

| | | | | |
|---|---|---|---|---|
| 7,247,873 | B2 * | 7/2007 | Arakawa | 250/583 |
| 2005/0280361 | A1 * | 12/2005 | Uhlig et al. | 313/504 |
| 2010/0039028 | A1 * | 2/2010 | Suzuki et al. | 313/504 |
| 2011/0204262 | A1 * | 8/2011 | Pu et al. | 250/492.1 |

* cited by examiner

*Primary Examiner* — Anastasia Midkiff
(74) *Attorney, Agent, or Firm* — Cha & Reiter, LLC

(57) ABSTRACT

A collimator for adjusting the shape of a region irradiated by radiation and a control method thereof. The collimator includes a plurality of irises to adjust the shape of the irradiation region, a light source outputting light to display the irradiation region, a reflective mirror to adjust a path of light radiated from the light source toward the irradiation region, and an image output unit outputting to the irradiation region a visible image representing the shape of a target object for radiography or a mark indicating the center of the radiation region.

23 Claims, 4 Drawing Sheets

COLLIMATOR AND CONTROL METHOD THEREOF

CLAIM OF PRIORITY

Pursuant to 35 U.S.C. §119(a), his application claims the benefit of the earlier filing date of Korean Patent Application No. 2011-0004558, filed on Jan. 17, 2011 in the Korean Intellectual Property Office and Korean Patent Application No. 2011-0073419, filed on Jul. 25, 2011 in the Korean Intellectual Property Office, the entire disclosure of both being incorporated herein by reference.

BACKGROUND

1. Field of the Invention

The present invention relates to a collimator which adjusts the shape of a region onto which radiation is directed and a control method thereof.

2. Description of the Related Art

An X-ray apparatus acquires an image within the body of an animal or a patient by irradiating the body with X-rays and then detecting X-rays that have passed through the body. Thereafter, the acquired image can be analyzed so as to enable detection of diseases within the body without an invasive procedure.

X-rays are electromagnetic waves having strong penetrating power which are discharged when electrons of a high speed collide with an object. An X-ray tube for generating X-rays generally includes a filament to discharge thermal electrons and electrodes to form a strong electric field in response to an applied high voltage. When a high voltage generated from a high voltage supply is applied to the X-ray tube, the filament forming a cathode discharges thermal electrons. The discharged thermal electrons drift under the influence of the applied high voltage so as to collide with an anode, and a spot having a local size on the anode where the thermal electrons collide, generates X-rays.

In general, an X-ray apparatus includes the above-described X-ray tube for generating X-rays, a collimator to adjust the shape of a region which the X-rays irradiate, and a detector to detect X-rays that have passed through an object.

The collimator to adjust the region which the X-rays irradiate blocks the radiated X-rays using a material which rapidly attenuates X-rays, such as tungsten, thus adjusting the shape of the irradiated region. The collimator typically also includes a structure to radiate visible light onto the same region as the region onto which the X-rays are radiated so as to enable a user to confirm the region onto which the invisible X-rays are radiated.

SUMMARY

Therefore, it is an aspect of the present invention to provide a collimator with an image output unit which forms a visible image representing the shape of an object to be photographed (i.e., imaged) or a mark indicating the center of a region onto which radiation is directed, and a control method thereof.

Additional aspects of the invention will be set forth in the description which follows and variations thereof will be obvious to those of ordinary skill in the art after reading this description.

In accordance with one aspect of the present invention, a radiation collimator includes a plurality of irises to adjust an irradiation region, a light source outputting light to display the irradiation region, a reflective mirror to adjust a path of light radiated from the light source, and an image output unit outputting an image representing the shape of a target object for radiography or a mark indicating the center of the irradiation region to the irradiation region.

The image output unit may include a display unit, and a control unit to visibly display the image representing the shape of the target object for radiography or the mark indicating the center of the irradiation region on the display unit, when information about the object for radiography is input from the outside.

The image output unit may be disposed in the path of light radiated from the light source.

The image output unit may be disposed outside of an irradiation path of the radiation used for the radiography.

The image output unit may include a liquid crystal display device or a micro emission device.

The micro emission device may use color filters.

The image output unit may be disposed in an irradiation path of the radiation used for the radiography.

The image output unit may include a film using transparent light emitting diodes.

The plurality of irises may be disposed on an irradiation path of the radiation.

The light source may be disposed outside of an irradiation path of the radiation so as to radiate visible light toward the reflective mirror.

The light source may include one selected from the group consisting of light emitting diodes, laser diodes, halogen lamps and xenon lamps.

The reflective mirror may be disposed in an irradiation path of the radiation.

In accordance with another aspect of the present invention, a control method of a collimator for adjusting the shape of an irradiation region includes determining an image corresponding to a target object for radiography, when information about the object for radiography is input, and transmitting a control signal to a display unit of the collimator to visibly display the determined image or a mark, indicating the center of a region onto which the radiation is radiated, on the display unit as well as on the irradiation region.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
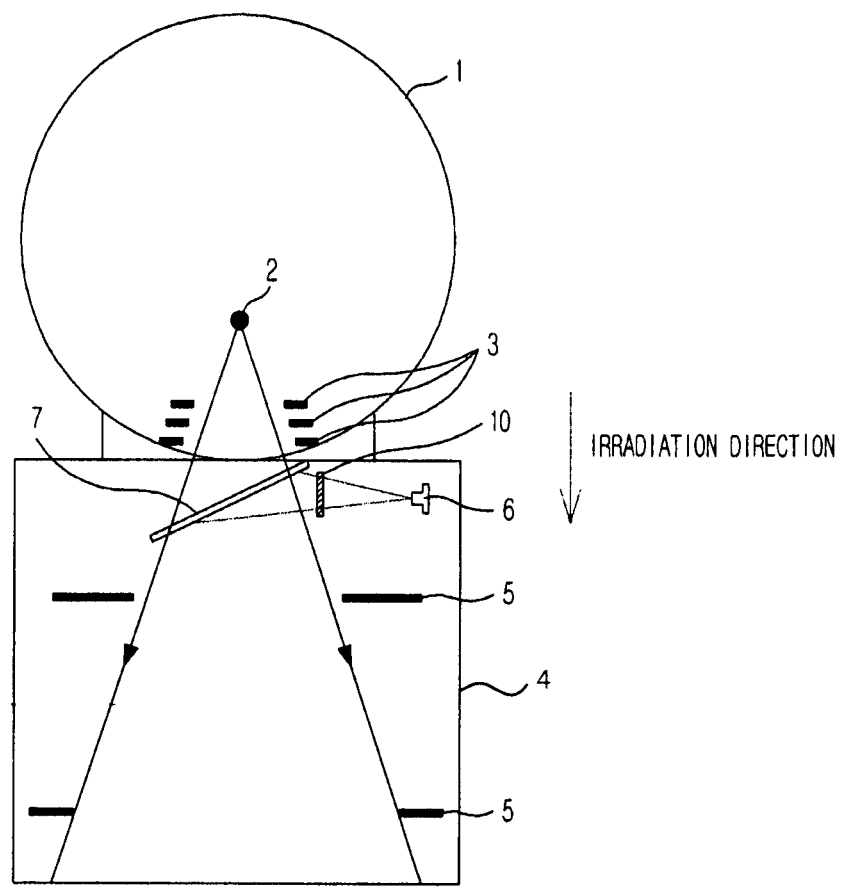
FIG. 1 is a schematic longitudinal-sectional view illustrating a radiation apparatus in accordance with one embodiment of the present invention.

Reference will now be made in detail to several embodiments of the present invention, examples of which are illustrated in the accompanying drawings, wherein like reference numerals refer to like elements throughout. However, it would be appreciated by those of ordinary skill in the art that changes may be made in these embodiments without departing from the principles and spirit of the invention, the scope of which is defined in the claims and their equivalents.

FIG. 1 is a schematic longitudinal-sectional view illustrating a radiation apparatus in accordance with one embodiment of the present invention.

The radiation apparatus in accordance with this embodiment includes a radiation generator 1 and a collimator 4 to adjust the shape of a path of radiation generated from the radiator generator 1 and a region onto which radiation generated from the radiation generator 1 is radiated.

Hereinafter, an X-ray apparatus will be exemplarily described as the radiation apparatus, and the region onto which radiation is radiated will be exemplarily described as the irradiation region.

The X-ray generator 1 generates electromagnetic waves having a short wavelength and strong penetrating power discharged when electrons of a high speed collide with an object, i.e., X-rays. The X-ray generator 1 may include a filament to discharge thermal electrons and electrodes to form a strong electric field in response to the application thereto of a high voltage.

When high voltage generated from a high voltage supply is applied to the X-ray generator 1, the filament forming a cathode discharges thermal electrons. The discharged thermal electrons drift under the influence of the strong electric field and collide with an anode, and a position of the anode having a local size with which the thermal electrons collide generates X-rays. With reference to FIG. 1, a portion denoted by reference numeral 2 represents the position of the anode having the local size with which the thermal electrons collide to generate X-rays.

The collimator 4 is disposed in front of the X-ray generator 1. The X-ray generator 1 may include irises 3 formed therein to adjust a radiation path of X-rays and a region onto which the X-rays are radiated so as to enable the X-rays to be directed toward the collimator 4.

The irises 3 may be formed of a material which may attenuate X-rays, such as lead or tungsten, but are not limited thereto.

The irises 3 may be operated in a manner of adjusting the region onto which the X-rays are radiated into a circular shape like an iris of a camera.

Further, the irises 3 may be operated in a manner of adjusting the region onto which the X-rays are radiated into a rectangular shape such that a pair of members formed of a material which may attenuate X-rays is bilaterally symmetrically arranged across a central axis for X-ray radiation and moves in the x-axis direction, i.e., rightward and leftward, and another pair of members is vertically symmetrically arranged across the central axis for X-ray radiation and moves in the y-axis direction, i.e., upward and downward. Such adjustment manners of the irises 3 are only exemplary and the irises 3 are not limited thereto.

After the radiation path and the irradiation region generated from the X-ray generator 1 are adjusted by the irises 3, the X-rays radiate toward the collimator 4 disposed in front of the X-ray generator 1.

The collimator 4 includes an iris 5 to adjust the shape of the radiation path and the irradiation region, a light source 6 to output visible light, a reflective mirror 7 to adjust a path of the visible light output from the light source 6, and an image output unit 10 to form an image in the irradiation region.

The iris 5 may adjust the shape of the radiation path and the irradiation region in the same manner as the irises 3 provided within the X-ray generator 1, as described above.

Since X-rays are invisible to the human eye, the shape of the irradiation region outside the collimator 4 is invisible to the naked eye. Therefore, the collimator 4 radiates visible light onto the irradiation region, thereby enabling a human to confirm the location and shape of the irradiation region with the naked eye.

The light source 6 radiates visible light toward the path along which the X-rays are radiated.

The light source 6 is switched on and off by a designated frequency. The light source 6 may use semiconductor light emitting devices, such as light emitting diodes (LEDs) or laser diodes (LDs), or gas discharge lamps, such as halogen lamps or xenon lamps, but is not limited thereto.

In order to enable the region onto which the X-rays are radiated to be visible to the human eye through visible light, the light source 6 outputting the visible light needs to be located at the same position as the generating position of the X-rays. However, since the light source 6 outputting the visible light is incapable of being arranged at the same position as the generating position of the X-rays (since it would block the X-rays, and also because it would be damaged by the X-rays), the light source 6 is provided outside of the irradiation path and radiates the visible light toward the radiation path of the X-rays, as shown in FIG. 1.

To this end, the reflective mirror 7 is disposed in the radiation path of the visible light radiated from the light source 6 and changes the direction of the radiation path of the visible light. In order to enable the irradiation region of visible light reflected by the reflective mirror 7 to coincide with the irradiation region of the X-rays, the reflective mirror 7 may be arranged at a designated angle with the radiation direction of the visible light. By changing the radiation path of the visible light using the reflective mirror 7, the irradiation region may be represented by the visible light.

The image output unit 10 is provided so as to form a visible designated image in the region onto which the X-rays are radiated.

It is noted that in this embodiment, the image output unit 10 is provided outside of the radiation path of the X-rays. The image output unit 10 may be provided between the light source 6 and the reflective mirror 7 so that the visible light radiated from the light source 6 passes through the image output unit 10 and then reaches the reflective mirror 7.

Figure 2:
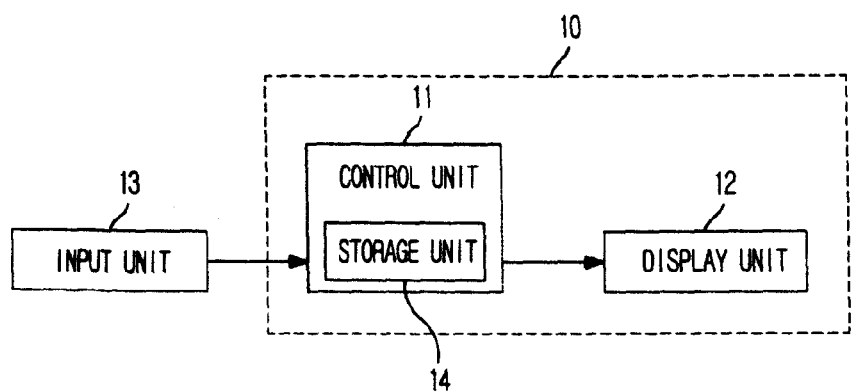
FIG. 2 is a block diagram illustrating the configuration of a collimator constructed and operating in accordance with one embodiment of the present invention.

The image output unit 10 may include a control unit 11 which selects a designated image corresponding to an object for photography by X-rays input from the outside through an input unit 13 according to information about the object for photography by X-rays and generates a control signal to display the image on a display unit 12, and the display unit 12 to display the image according to the control signal of the control unit 11 (with reference to FIG. 2).

When information about a designated part of the object for photography by X-rays is input from the outside, the control unit 11 selects one designated image corresponding to the information from among a plurality of images stored in advance in a storage unit 14 according to the input information.

For example, the control unit 11 may select a designated image representing the shape of a hand of a human from among the plural images stored in the storage unit 14 when information that a hand of a patient is to be photographed by X-rays is input, select a designated image representing the shape of the whole body of a human from among the plural images stored in the storage unit 14 when information that the whole body of a patient is to be photographed by X-rays is input, and select a designated image representing the shape of the upper body of a human from among the plural images stored in the storage unit 14 when information that the chest of a patient is to be photographed by X-rays is input. Here, the plural images may be predetermined based on information about body parts of a human that are typically photographed by X-rays using such X-ray apparatus, and be expressed as images representing the shapes of the body parts of a person which is photographed by X-rays.

When the designated image corresponding to the information about the part to be photographed by X-rays is selected from the plural images stored in the storage unit 14, the control unit 11 outputs a control signal to control operation of the display unit 12 so as to display the image on the display unit 12. Further, the control unit 11 outputs a control signal to control operation of the display unit 12 so as to display a mark, indicating the center of the region onto which X-rays are to be radiated, on the display unit 12. Because the visible light from source 6 passes through display unit 12 while it is displaying both the designated image and mark, the radiation of this visible light through the collimator 4 and ultimately onto the irradiation region, serves to enable the center of the region onto which X-rays are radiated to be easily and confidently recognized from the outside. The mark indicating the center of the radiation region may have a cross shape, but is not limited thereto.

The display unit 12 displays the selected designated image according to the control signal output from the control unit 11. Further, the display unit 12 displays the mark indicating the center of the irradiation region according to the control signal output from the control unit 11.

The display unit 12 may display the image using a liquid crystal display device or a micro emission device using color filters, but is not limited thereto.

When the designated image selected by the control unit 11 and the mark indicating the center of the irradiation region are displayed on the display unit 12, after the visible light passes through the image output unit 10, the visible light is reflected by the reflective mirror 7 and ultimately reaches the irradiation region, where the irradiation region is made to be visible to the naked eye due to the passage through the collimator of the visible light, and the designated image displayed by the image output unit 10 is projected onto the irradiation region and displayed, simultaneously therewith. Furthermore, together with the display of the designated image, the mark indicating the center of the irradiation region is projected onto the irradiation region and displayed. Both the image and the mark indicating the center of the irradiation region or either the image or the mark indicating the center of the irradiation region may be displayed in the irradiation region according to a preferred selection indicated by a user operating the radiation apparatus. A patient undergoing X-ray photography may check the image projected onto the irradiation region and the mark indicating the center of the irradiation region of the X-rays, and then re-position his/her body part based on the position of the projected image and/or mark.

Figure 3:
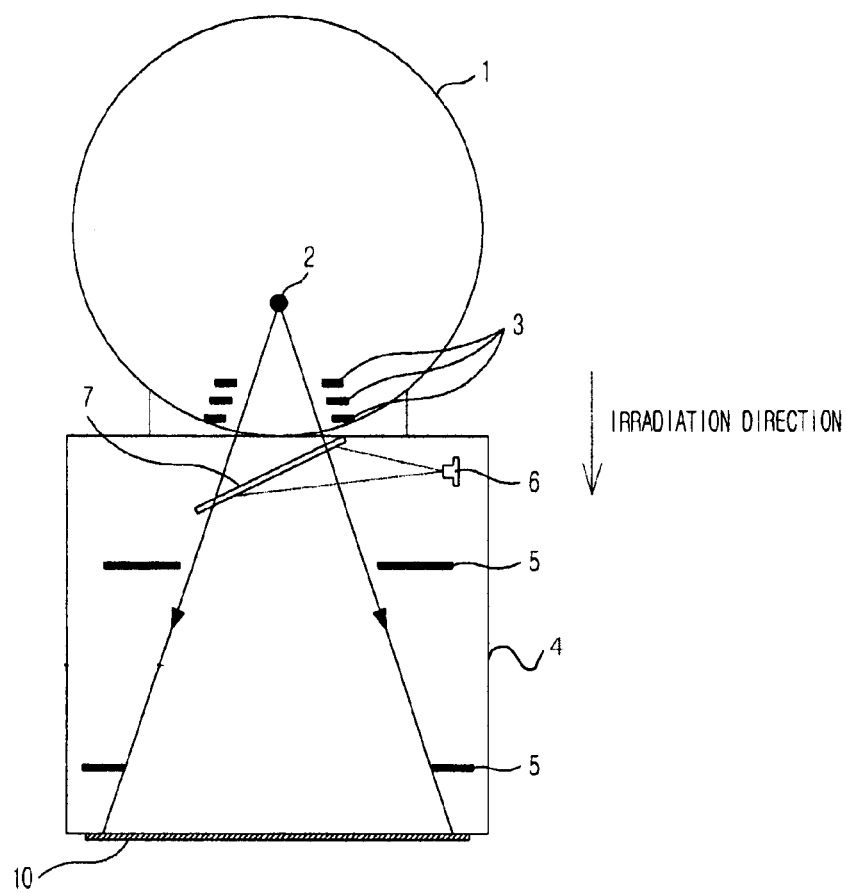
FIG. 3 is a schematic longitudinal-sectional view illustrating a radiation apparatus constructed and operating in accordance with another embodiment of the present invention.

FIG. 3 is a schematic longitudinal-sectional view illustrating a radiation apparatus in accordance with another embodiment of the present invention.

The radiation apparatus in accordance with this embodiment includes a radiation generator 1 and a collimator 4 to adjust the shape of a radiation path of radiation generated from the radiator generator 1 and an irradiation region onto which radiation generated from the radiation generator 1 is radiated.

Hereinafter, an X-ray apparatus will be exemplarily described as the radiation apparatus.

The X-ray generator 1 in accordance with this embodiment is the same as the X-ray generator 1 of FIG. 1, and a detailed description thereof will thus be omitted.

The collimator 4 includes an iris 5 to adjust the shape of an irradiation region onto which X-rays are radiated, a light source 6 to output visible light, a reflective mirror 7 to adjust a path of the visible light output from the light source 6, and an image output unit 10 to form a visible image in the irradiation region onto which the X-rays are radiated.

The iris 5, the light source 6 and the reflective mirror 7 are the same as those of FIG. 1, and a detailed description thereof will thus be omitted.

The image output unit 10 forms a designated image in the irradiation region.

Although FIG. 3 illustrates the image output unit 10 as being disposed on a discharge surface of collimator 4 through which the X-rays and the visible light are discharged to the outside from the collimator 4, the image output unit 10 may be provided at other positions on an radiation path through which both the X-rays and the visible light pass. In order to display the irradiation region, the visible light output from the light source 6 passes through the image output unit 10 provided on the radiation path and then the visible light is radiated to the outside of collimator 4.

The image output unit 10 includes, in the same manner as the image output unit 10 of FIG. 1, a control unit 11 which selects a designated image corresponding to external input from among plural images stored in advance in a storage unit 14 according to the external input and generates a control signal to display the image on a display unit 12, and the display unit 12 to display the image according to the control signal of the control unit 11 (with reference to FIG. 2).

The display unit 12 may display the image using a film employing transparent light emitting diodes, but is not limited thereto.

The remaining description of the control unit 11 and the display unit 12 of the image output unit 10 is the same as that of FIG. 1, thus being omitted.

Figure 4:
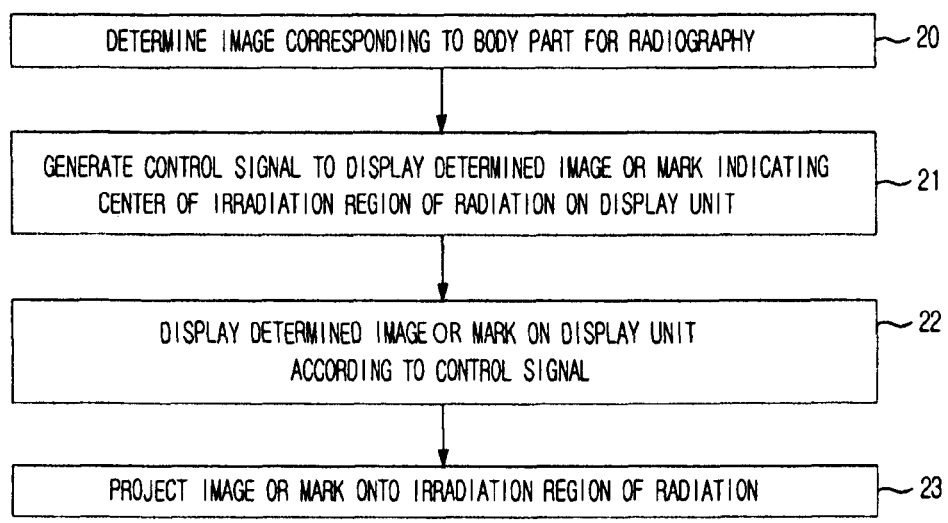
FIG. 4 is a flowchart illustrating a control method of a collimator in accordance with one embodiment of the present invention.

FIG. 4 is a flowchart illustrating a control method of a collimator in accordance with one embodiment of the present invention.

As shown in FIG. 4, the image output unit 10 determines an image corresponding to a body part of a patient to be photographed (Operation 20).

When information about the body part of the patient to be photographed is input from the outside, the control unit 11 of the image output unit 10 determines a designated image corresponding to the information from among plural images stored in advance in the storage unit 14 according to the input information. Here, the plural images may be predetermined based on information about body parts of a human such as typically photographed by radiation and be expressed as images representing the shapes of the body parts of a patient which is photographed.

When the designated image corresponding to the body part of the patient to photographed from among the plural images stored in the storage unit 14 is determined, the control unit 11 outputs a control signal to display the designated image and/or a mark indicating the center of the irradiation region on the display unit 12 to the display unit 12 (Operation 21). Both the image and the mark indicating the center of the irradiation region or either the image or the mark indicating the center of the irradiation region may be displayed according to a preferred selection of a user operating the radiation apparatus. Here, display of both the image and the mark indicating the center of the irradiation region will be exemplarily described.

When the control signal is output to the display unit 12, the display unit 12 displays the designated image and the mark indicating the center of the irradiation region according to a control signal (Operation 22). The display unit 12 may display the designated image using a liquid crystal display device or a micro emission device using color filters, or display the image using a film using transparent light emitting diodes.

When visible light passes through the image output unit 10 on which the designated image and the mark indicating the center of the irradiation region are displayed, the corresponding image and the mark indicating the center of the irradiation region are visibly projected onto and displayed in the irradiation region (Operation 23).

When the image and the mark indicating the center of the irradiation region are displayed in the irradiation region, the patient undergoing radiography may check the position of the image projected onto the irradiation region and the mark indicating the center of the irradiation region, and re-position his/her body part based on the position of the projected image.

As is apparent from the above description, a collimator in accordance with one embodiment of the present invention forms an image to guide a position and a posture of a patient into a region in which radiation is to be radiated, thereby more precisely and easily executing radiography.

Furthermore, the collimator in accordance with one embodiment of the present invention enables the patient himself/herself to correct his/her posture according to the image formed in the irradiation region, thereby more rapidly executing radiography.

Although a various embodiments of the present invention have been shown and described, it would be appreciated by those of ordinary skill in the art that changes may be made in these embodiments without departing from the principles and spirit of the invention, the scope of which is to be defined only by the following claims and their equivalents.

What is claimed is:

1. A collimator for adjusting an irradiation field of radiation to be used for radiography, comprising:
    a plurality of irises for adjusting a shape of a radiation path of X-rays and an irradiation region onto which the X-rays are radiated;
    a light source outputting visible light to display the irradiation region;
    a reflective mirror to adjust a path of light radiated from the light source; and
    an image output unit responsive to visible light output from the light source for outputting data in accordance with a user selection representing a designated image showing a representative shape of a target object for radiography.

2. The collimator according to claim 1, wherein the irradiation region is represented by the visible light and the image output unit includes:
    a display unit; and
    a control unit to display on the display unit the image representing the shape of the target object for radiography, when information about the object for radiography is input to the control unit.

3. The collimator according to claim 1, wherein the image output unit is disposed in the path of light radiated from the light source.

4. The collimator according to claim 1, wherein the image output unit is disposed outside of a radiation path of the radiation.

5. The collimator according to claim 4, wherein the image output unit includes a liquid crystal display device or a micro emission device.

6. The collimator according to claim 5, wherein the micro emission device uses color filters.

7. The collimator according to claim 1, wherein the image output unit is disposed in a radiation path of the radiation.

8. The collimator according to claim 7, wherein the image output unit provides an image using light emitting diodes.

9. The collimator according to claim 1, wherein the plurality of irises are disposed in a radiation path of the radiation.

10. The collimator according to claim 1, wherein the light source is disposed at the outside of radiation path to radiate visible light toward the reflective mirror.

11. The collimator according to claim 1, wherein the light source includes one selected from the group consisting of light emitting diodes, laser diodes, halogen lamps and xenon lamps.

12. The collimator according to claim 1, wherein the reflective mirror is disposed in a radiation path of the radiation.

13. The collimator according to claim 1, wherein the plurality of irises adjust a shape of the irradiation region.

14. A method of control of a collimator for adjusting an X-ray irradiation region of radiation, the control method comprising:
    determining an image corresponding to a target object for radiography, in response to input of information about the object;
    outputting visible light to show an X-ray irradiation region; and
    transmitting a control signal to a display unit to cause the display unit to visibly display in accordance with a user selection a designated image comprising the visible light showing a representative shape of the target object for radiography.

15. The method of claim 14, further comprising:
    outputting visible light through the display unit, so as to cause display in the irradiation region of a visible image representing the shape of the target object for radiography.

16. The method of claim 15, wherein outputting visible light, comprises:
    providing a light source outside a path of the radiation that is shaped by the collimator, and
    providing a mirror inside the path of the radiation that is shaped by the collimator so as to reflect the visible light output by the light source onto the irradiation region.

17. The method of claim 15, further comprising providing the display unit of the collimator outside a path of the radiation that is shaped by the collimator.

18. The method of claim 15, further comprising providing the display unit of the collimator inside a path of the radiation that is shaped by the collimator.

19. The method of claim 16, further comprising providing the display unit of the collimator outside the path of the radiation that is shaped by the collimator.

20. The method of claim 16, further comprising providing the display unit of the collimator inside the path of the radiation that is shaped by the collimator.

21. The method of claim 14, further comprising providing an image using light emitting diodes as an image output unit.

22. The collimator according to claim 1, wherein the image output unit shows a mark indicating a center of the irradiation region.

23. The method of claim 14, further comprising:
    transmitting a control signal to a display unit to cause the display unit to visibly display a mark indicating a center of a region onto which the radiation is to be radiated.

* * * * *